United States Patent [19]
Wilson et al.

[11] Patent Number: 5,989,198
[45] Date of Patent: Nov. 23, 1999

[54] USE OF CAPILLARY ELECTROPHORESIS TO DETERMINE GLOMERULAR FILTRATION RATE USING IOTHALAMATE

[75] Inventors: David M. Wilson; Jan H. Bergert, both of Rochester, Minn.; James P. Landers, Pittsburgh, Pa.; Robert R. Liedtke, Kasson, Minn.

[73] Assignee: Mayo Foundation for Medical Education and Research, Rochester, Minn.

[21] Appl. No.: 08/866,575

[22] Filed: May 30, 1997

[51] Int. Cl.$^6$ ........................................................ A61B 5/00
[52] U.S. Cl. ............................................................. 600/584
[58] Field of Search ..................................... 600/573, 584; 73/64.58, 861, 861.05, 861.07; 604/20

[56] References Cited

PUBLICATIONS

Al–Uzri, A., et al., "An Accurate Practical Method for Estimating GFR in Clinical Studies Using a Constant Subcutaneous Infusion", *Kidney Intl.*, 41, 1701–1706, (1992).

Bajaj, G., et al., "125–Iodine–iothalamate clearance in children. A simple method to measure glomerular filtration", *Ped. Nephrology*, 10, 25–28, (1996).

Brochner–Mortensen, Jr., et al., "Renal Inulin Clearance versus Total Plasma Clearance of 51–Cr–EDTA", *Scand. J. Clin. Lab. Invest.*, 23, 301–305, (1969).

Brown, S.C., et al., "Iohexol Clearance for the Determination of Glomerular Filtration Rate in Clinical Practice: Evidence for a New Gold Standard", *J. of Urology*, 146, 675–679, (1991).

Bubeck, B., et al., "A new principle to normalize plasma concentrations allowing single–sample clearance determinations in both children and adults", *Eur. J. on Nucl. Med.*, 19, 511–516, (1992).

Gaspari, F., et al., "Measurement of GFR with a single intravenous injection of nonradioactive iothalamate", *Kidney Int.*, 41, 1081–1084, (1992).

Gaspari, F., et al., "Plasma Clearance of Nonradioactive Iohexol as a Measure of Glomerular Filtration Rate", *J. of Am. Soc. of Nephrology*, 6, 2, 257–263, (1995).

Gordon, M.J., et al., "Capillary Electrophoresis", *Science*, 242, 224–228, (1988).

Holliday, M.A., et al., "Serial Measurements of GFR in Infants Using the Continuous Iothalamate Infusion Technique", *Kidney Intl.*, 43, 839–898, (1993).

Isaka, Y., et al., "Modified Plasma Clearance Technique using Nonradioactive Iothalamate for Measuring GFR", *Kidney Intl.*, 42, 1006–1011, (1992).

Israelit, A.H., et al., "Measurement of Glomerular Filtration rate Utilizing a single Subcutaneous Injection of 125–I–iothalamate", *Kidney Intl.*, 4, 346–349, (1973).

Jacobsson, L., "A Method for the Calculation of Renal Clearance Based on a Single Plasma Sample", *Clin. Physiology*, 3, 297–305, (1983).

O'Reilly, P.H., et al., "Measurement of the Plasma Clearance of Urographic contrast Media for the Determination of Glomerular Filtration Rate", *J. of Urology*, 139, 9–11, (1988).

Ott, N.T., et al., "A simple technique for estimating glomerular filtration rate with subcutaneous injection of [125I] Iothalamate", *Mayo Clinic Proceedings*, 50, 664–668, (1975).

Price, M., "Comparison of Creatinine Clearance to Inulin Clearance in the Determination of Glomerular Filtration Rate", *J. Urol.*, 107, 339–340, (1972).

(List continued on next page.)

*Primary Examiner*—Max Hindenburg
*Attorney, Agent, or Firm*—Schwegman, Lundberg, Woessner & Kluth, P.A.

[57] ABSTRACT

A method is provided to determine glomerular filtration rate employing capillary electrophoresis to measure the concentration of a non-labeled iothalamic acid salt in urine and blood samples.

21 Claims, 3 Drawing Sheets

OTHER PUBLICATIONS

Prueksaritanont, T., et al., "Simple and micro high–performance liquid chromatographic method for simultaneous determination of a–aminohippuric acid and iothalamate in biological fluids", *J. of Chromatoraphy,* 30X, 89–97, (1984).

Rocco, M.V., et al., "Capillary electrophoresis for the determination of glomerular filtration rate using nonradioactive iohexol", *Am. J. of Kidney Diseases,* 28, 2, 173–177, (1996).

Rocco, M.V., et al., "Measurement of glomerular filtration rate using nonradioactive iohexol: Comparison of two One–Compartment models", *Am. J. of Nephrology,* 16, 138–143, (1996).

Shihabi, Z.K., "Clinical Applications of Capillary Electrophoresis", *Ann. of Clin. and Lab. Sci.,* 22, 6, 398–405, (1992).

Shihabi, Z.K., et al., "Iohexol in serum determined by capillary electrophoresis", *Clin. Chem.,* 38, 10, 2117–2120, (1992).

USE OF CAPILLARY ELECTROPHORESIS TO DETERMINE GLOMERULAR FILTRATION RATE USING IOTHALAMATE

BACKGROUND OF THE INVENTION

The measurement of glomerular filtration rate (GFR) is an important index in the evaluation and follow-up of patients with renal disease and transplant recipients. Rigorous assessment of the glomerular filtration rate has been accomplished by measurement of the renal clearance of inulin, a fructose polymer that fulfills the criteria for a filtration marker. See M. Price, *J. Urol.*, 107, 339 (1972). However, the classical inulin clearance method is not suitable for routine clinical purposes, since it requires continuous infusion and, sometimes, bladder catheterization of the patients. H. W. Smith, in The Kidney: Structure and Function in Health and Disease, H. W. Smith, ed., Oxford University Press, NY (1951) at pages 39–62.

More precise evaluation of renal function has been determined by infusion of $^{51}$Cr-EDTA and $^{125}$I-iothalamate. However, radioactive exposure, appropriate handling, disposal of radioactive materials, and cost (in part related to deterioration and limited shelf life of radioisotopes) has limited the use of radioisotopes. See, J. Brochner-Mortensen et al., *Scand. J. Clin. Lab. Invest.*, 23, 301 (1969); G. Bajaj et al., *Pediatr. Nephrol.*, 10, 25 (1996); and A. H. Israelit et al., *Kid. Int.*, 4, 346 (1973).

Attempts to avoid exposure to radioisotopes have led to the investigation of new techniques for measuring GFR, and several methods have been developed for measurement of iothalamate using HPLC determinations. See, for example, A. Al-Uzri et al., *Kid. Int.*, 41, 1701 (1992); T. Prueksaritanont et al., *J. Chrom.*, 306, 89 (1984); M. A. Holliday et al., *Kid. Int.*, 41, 1701 (1992). These methods avoid radioisotopes but are labor intensive. Therefore, they are not widely accepted for routine use.

Other methods have focused on x-ray fluorescence of iohexol for measurement of serum concentration and estimated plasma clearance with a one or two blood sample technique. The iohexol technology using the Renalyzer avoids radioisotope problems but is less sensitive, requiring relatively large doses of the injected drug in order to measure GFR. See, for example, S. C. W. Brown et al., *J. Urol.*, 146, 675 (1991).

Rocco et al., *Am. J. Nephrol.*, 16, 138 (1996), recognized the advantage of HPLC for measuring iohexol in order to use relatively smaller sample volumes. This method, however, is labor intensive and time consuming. Because of the perceived limitations of both the x-ray fluorescence and HPLC, Rocco et al., *Am. J. Kid. Dis.*, 28, 173 (1996), investigated the applicability of capillary electrophoresis (CE) for the determination of serum iohexol. They reported utilization of capillary electrophoresis using a relatively large (5 ml) dose of injected iohexol to evaluate a monoexponential disappearance curve for determination of GFR in patients. Clearances using this method were compared with the "standard" clearance of $^{125}$I-iothalamate and iohexol measured by an HPLC method.

However, a continuing need exists for simple methods to accurately measure GFR using non-radioactive tracers in small doses.

SUMMARY OF THE INVENTION

The present invention provides a method for using capillary electrophoresis to determine glomerular filtration rate (GFR) using a non-radioactive iothalamic acid salt. The method can be carried out using a single subcutaneous injection of the iothalamic acid salt, preferably iothalamate meglumine, followed by the determination of the average plasma level of the iothalamic acid salt during one period of urine collection. The timed urine collection is used to determine urinary flow rate, and the urine is sampled to determine the urinary level of the iothalamic acid salt. These parameters permit the calculation of GFR, which then can be corrected for the body area of the subject.

More specifically, the present invention provides a method for determining glomerular filtration rate in a mammal, such as a human, comprising: (a) subcutaneously administering, as by injection, to said human an effective detection amount of a non-radiolabeled iothalamic acid salt, such as iothalamate meglumine; (b) measuring the volume of urine produced by said human over a preselected period of time following said administration; (c) obtaining a sample of blood plasma from said human at about the midpoint of said period of time; (d) employing capillary electrophoresis to measure the concentration of said iothalamic acid salt in said plasma sample and in a sample of said urine; (e) determining said urinary flow rate over said period of time; and (f) calculating the glomerular flow rate by dividing the concentration of said iothalamic acid salt in said urine sample multiplied by said urinary flow rate by the concentration of said iothalamate meglumine in said plasma sample.

Preferably, the average plasma level of the iothalamic acid salt (the marker) is determined by obtaining a first blood plasma sample following administration of the marker, but after the blood level of the marker has peaked, i.e., after equilibration. The urine output is then measured over a preselected period of time, to determine urinary flow rate, and sampled. A second blood plasma sample is then obtained, following bladder emptying, and the average concentration of the marker in the two plasma samples is determined using CE to measure the marker concentration in each sample.

Preferably, the subject is hydrated by administration of water, i.e., orally, prior to injection of the marker, and hydration can be continued throughout the period of urine flow measurement and collection. Preferably, the GFR is corrected for the body surface area of the subject as disclosed below. The plasma and urine samples are preferably deproteinized prior to CE analysis. Control blood and urine samples can also be obtained prior to marker injection, and assayed by CE for the presence of analytes, such as drugs, that might interfere with the measurement of the iothalamic acid salt.

Since not all medical facilities possess the analytical and data processing equipment required to carry out the analysis of marker levels by capillary electrophoresis, the present invention also provides a kit for sampling human physiological fluids to determine glomerular filtration rate comprising packaging containing: (a) container adapted to contain a blood sample; (b) a second container adapted to contain a urine sample; and (c) a third container containing an amount of an iothalamic acid salt, such as iothalamate meglumine, in combination with a pharmaceutically acceptable liquid carrier. The kit can further comprise a second container adapted to contain a second blood sample, and, optionally, a fourth container containing a pH 11–11.5 borate buffer.

The kit can also contain instruction means, such as a package insert, labeling, a cassette tape or a videotape directing the user to administer the iothalamic acid salt, to collect blood and urine samples and to determine urinary flow rate, in accord with the present method. The blood sample(s) and urine sample are then mailed to a central facility that processes them as necessary and determines the concentrations of marker in each sample and calculates the GFR (corrected and uncorrected) as disclosed herein. The term "blood" as used with respect to the present kit includes whole blood, blood plasma or serum.

DETAILED DESCRIPTION OF THE INVENTION

Capillary Electrophoresis

Figure 1:
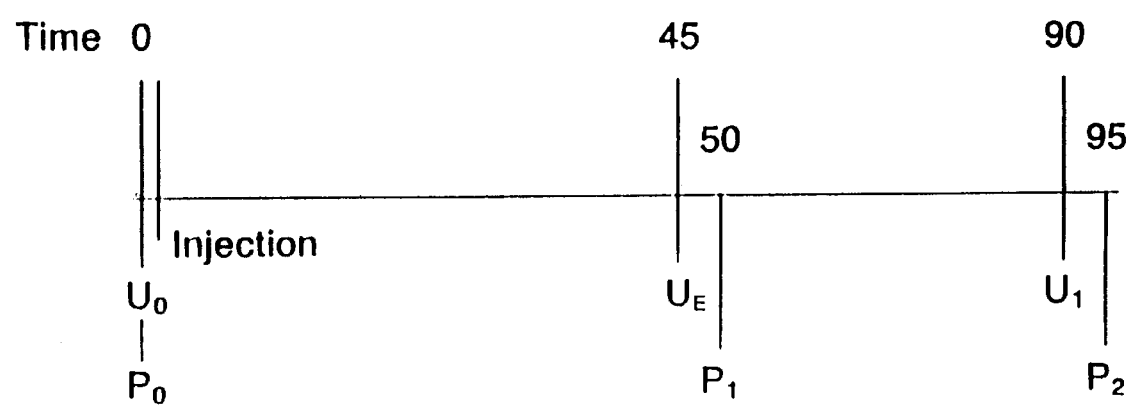
FIG. 1 schematically depicts the time course for subcutaneous injection of isotopic and cold iothalamate and collection of blood (P) and urine (U) samples; time is in minutes.

Electrophoresis is an electrified-driven process in which molecules with a net charge migrate in a solution under the influence of an electric current. Capillary electrophoresis (CE) uses an open capillary tube, i.e., a tube typically made of fused silica containing a buffer without a stabilizing medium, such as a gel. In such a system, electrophoresis can take place with minimal interference and zone broadening can be minimized. The capillary acts like the microphorous gel to counteract convective flow. Thus, the stabilizing effect of the capillary increases as the capillary diameter is decreased. This decrease in diameter of the capillary increases the surface to volume ratio and thus enhances heat dissipation.

In capillary electrophoresis, a buffer-filled capillary is suspended between two reservoirs filled with buffer. Typical capillary internal diameters are about 20–200 µm, i.e., often less than 80 microns across, and typical lengths are from 10 cm to more than one meter. A high voltage power supply (10–30 kV) applies an electric field across the two ends of the capillary. Samples are introduced at the inlet end, which, under the influence of the electrical field with normal polarity (inlet+, outlet−) will be swept towards the detection/outlet end of the capillary by endoosmotic flow. When the analytes comprising the sample migrate through the detector part of the capillary, an electronic record of the number of analyte components and their concentration is stored. Typically, ultraviolet-visible (UV-vis), fluorescent, or conductivity detection methods are used for detection.

In capillary zone electrophoresis (CZE), a sample zone migrates with a carrier electrolyte. The carrier constituents have the same charge as the sample constituents to be separated. The walls of fused silica capillaries have a negative charge in aqueous solution from the ionization of surface silanol groups. When a voltage is applied, a bulk flow of fluid toward the cathode occurs. This is electroosmotic flow, which is caused by the electrical double layer formed at the wall-electrolyte interface. A positively charged sample component emerges early because both the electrophoretic motion of the ion and the electroosmotic motion of the electrolyte are in the same direction. If the component is negatively charged, but its electrophoretic mobility is less than the electroosmotic mobility, then that component also migrates toward the cathode but at a lower rate. Thus, separations are based upon differences in the electrophoretic mobilities of the constituents, and significantly high resolution separations can be obtained and manipulated by changing the electrophoretic medium (e.g., pH and buffer composition), as discussed hereinbelow. Sample volumes can be lowered to the nl or pl range, and detection volumes can be as small as 30 pl or less.

See also, M. J. Gordon et al., *Science*, 242, 224 (1988); Z. K. Shihabi et al., *Clin. Chem.*, 38, 2117 (1992) and Z. K. Shihabi, *Ann. Clin. Lab. Sci.*, 22, 398 (1992).

Iothalamic Acid Salts

Iothalamic acid (5-acetamido-2,4,6-triiodo-N-methylisophthalamic acid) is described in *The Merck Index* (11th ed., 1989) at entry 4952, along with the n-methylglucamine salt (iothalamate meglumine) and the $^{131}$I-labeled sodium salt (Conray®-400). Iothalamate meglumine is commercially available as Conray® from Mallinckrodt Medical Inc., St. Louis, Mo. Iothalamate meglumine is readily detectable in aqueous buffers using UV detection at 254 nm. Other non-radioactive pharmaceutically acceptable iothalamic acid salts can be used in the present methods and kits, including acid addition salts of other nontoxic amines and alkali metal salts.

As used herein, the term "effective diagnostic amount" of an iothalamic acid salt is an amount that when administered to a mammal subcutaneously, as by injection, infusion, iontophoresis etc., yields blood and urine concentrations that are detectable by CE at levels that are useful to calculate GFR. A preferred effective diagnostic amount of iothalamate meglumine for a human weighing ≧20 kg is a unit dose of about 250–350 mg, and an effective diagnostic amount for a human weighing <20 kg is about 150–200 mg.

The iothalamic acid salt is preferably provided and administered in combination with a pharmaceutically acceptable liquid vehicle, such as a physiological salt solution, a buffer, and the like, which may contain minor but effective solubilizing amounts of alcohols, glycols, polyols and the like.

The present invention will be further described by reference to the following detailed example, wherein iothalamate [60% iothalamate meglumine (Conray®; 1-deoxy-1-(methylamino)-D-glucitol-5-acetamido-2,4,6,-triiodo-N-methylisophthalamate)] was obtained from Mallinckrodt Medical, Inc. (St. Louis, Mo.) as a sterile aqueous solution used as a diagnostic radiopaque medium containing 282 mg/mL organically bound iodine. A.C.S. reagent grade sodium tetraborate decahydrate was purchased from Aldrich Chemical Co., Inc. (Milwaukee, Wis.); sodium hydroxide (1.0 N and 0.1 N) were from Mallinckrodt Baker, Inc. (Phillipsberg, N.J.). Microcon-10 ultrafilters were from Amicon Inc. (Beverly, Mass.). Polyimide-coated fused silica capillary, 50 µm i.d.; 360 µm o.d., was purchased in bulk from Polymicro Technologies, Inc. (Phoenix, Ariz.). The separation buffer is 50 mM borate (12.5 mM sodium tetraborate decahydrate). An aliquot of this stock is adjusted daily to pH 11.25–11.30 using 1.0 N NaOH. The sample and standard diluting buffer is 5 mM borate made from the 50 mM borate stock, diluted 1:10 with distilled deionized water and adjusted to pH 11.25–11.30 using 1.0 N NaOH, which is prepared monthly.

Capillary electrophoresis separations were performed on a Beckman P/ACE 2100 (UV detection at 254 nm). Instrument control, data collection and analysis were accomplished through Beckman System Gold software (V. 7.12;

Beckman Instruments Inc., Fullerton, Calif.). All migration times and peak areas were obtained through the System Gold software.

Prior to use, the capillary was conditioned with 20 minute rinses (100 capillary volumes; 20 psi or 138 KPa) of the following: 1) 0.1 N NaOH: 2) distilled deionized water; 3) 50 mM borate buffer. The capillary is ready for use at this point. It can be rinsed for 10 minutes with distilled deionized water, capped at both ends, and stored at 4° C. with water in the capillary.

EXAMPLE 1

Measurement of GFR Using $^{125}$I-iothalamate and Iothalamate Meglumine

A. Patient Preparation

One hundred Mayo Clinic Renal Laboratory patients were initially recruited for measurement of GFR using $^{125}$I-iothalamate (Glofil®, Isotex Diagnostics, Friendswood, Tex.) and "cold" iothalamate meglumine. Subsequently, 31 additional patients were recruited after the initial data set was evaluated, and a minor technical change in sample handling was performed, as discussed below. Informed consent was obtained. The age range was 23 to 82 years. Women with any question of pregnancy were tested prior to the study. Pregnant or lactating women were not used for this study because of the "standard" isotopic techniques used.

Prior to the test, patients were given 3 drops of a saturated solution of potassium iodide in 20 mls of water to prevent thyroid uptake of the small amount of free $^{125}$I-iothalamate and to protect patients from radiation exposure to the thyroid. They were also given a single subcutaneous injection of 0.5 mls of iothalamate meglumine (Conray®) (300 mg) diluted 1:1 with distilled water. Patients who professed an allergy to iodine were not included in this study, nor were patients who had been given an angiographic dye in the previous 24 hours.

B. Performance of the Test

On the day of the appointment, the patient ate nothing for 4 hours preceding the test (diabetics 2 hours) and drank 4 glasses of water in the hour preceding the test. They were also instructed not to void within 45 minutes of their appointment time. Patients were given oral hydration of 200 mls/per hour throughout the test.

Prior to injection, urine ($U_0$) and blood plasma ($P_0$) samples were obtained to assess for drug interferences. After subcutaneous injection of the two different GFR markers, a 45-minute equilibration period allowed blood levels to peak and become stable or fall as previously described for 125I subcutaneous iothalamate clearances by N. T. Ott et al., *Mayo Clin. Proc.*, 50, 664 (1975), for $^{125}$I-iothalamate. This sampling method was adapted from studies reported by Israelit et al. for $^{125}$I-iothalamate, in *Kid. Int.*, 4, 346 (1973). After the 45 minute equilibration period, 7 ml of blood ($P_1$) and a urine sample ($U_E$) were collected and time ($T_0$) was recorded. The urine ($U_E$) passed at 45 minutes was discarded. Bladder emptying was assessed by monitoring with a Diagnostic Ultrasound bladder scanner (Model No. 2500). If the bladder was not empty after voiding at 45 minutes, the study was extended for 30 minutes and the patient voided again. Three patients required catheters to assure emptying when this failed. Blood samples were obtained within 5 minutes of a successfully voided urine.

The patient was moved to a waiting room and returned to the laboratory after 45 to 60 minutes when the urge to void became apparent. Second blood ($P_2$) and urine ($U_1$) samples were collected, urine volume was recorded, and bladder emptying monitored. Adequacy of the test was confirmed if the bladder was empty (<10 ml or <10% of voided volume on scanner readout), and a minimum of 100 mls of urine was voided during the test. The timed urine ($U_1$) and bloods ($P_1$ and $P_2$) were analyzed by CE.

C. Drug Doses and Sample Handling

The dose for the "cold" iothalamate was 300 mg for patients >20 kg given subcutaneously in the upper outer arm. The bladder scanner was calibrated weekly with a phantom with tolerances of ±10%. Electronic balances for measuring urine volume were calibrated daily with 500 gm and 1000 gm weights, tolerance to 0.5 gms. Instrument calibration was documented daily.

$^{125}$I-iothalamate was injected subcutaneously, 20 $\mu$Ci/70 kg, at a separate site in the same arm. Seven mls of blood were drawn into 10 mls sodium heparin vacutainers, centrifuged 7 minutes at 1000 RCF, and separated from cells (0.3 mls plasma necessary for CE). $U_1$ was collected, the exact time recorded, volume was measured by weight, and a 5 ml aliquot was retained for analysis. The aforementioned samples were used for isotope measurement and, subsequently, for "cold" iothalamate measurements.

D. Sample Preparation and CE Analysis

Two mls of plasma and urine ($U_1$, $P_1$, $P_2$) obtained from subjects treated with $^{125}$I-iothalamate, were sufficient to get 10,000 counts on a Packard Minaxi Series 5000 gamma counter. Counts per minute (CPM)/2.0 ml were determined and clearances calculated as previously described by Ott et al., cited above.

Capillary electrophoresis technology for measuring cold iothalamate was performed as follows: Plasma was deproteinized after combining 300 $\mu$L of plasma from $P_1$ and $P_2$ One hundred $\mu$L of the plasma pool was put into a micron ultrafilter (Amicon) (MWCO 10,000) and centrifuged 10 minutes at 14,000 RCF. (For the last 31 cases, the ultrafiltrate was also mixed on a vortex mixer before sampling.) Three hundred $\mu$L of $U_1$ and $U_0$ were put onto the Amicon filter and centrifuged 10 minutes at 14,000 RCF. The urine was diluted with a Beckman Accuprep diluter with 5 mM borate solution, pH 11.3. $U_0$ was diluted 1:30; $U_1$ was diluted 1:5 or 1:10. Deproteinized plasma was run undiluted.

Standards and samples were loaded into a polyimide-coated fused silica capillary by pressure injection. The buffer was 50 mM borate at pH 11.3 (pH adjusted with 1.0 N NaOH) which was prepared fresh daily from a stock 50 mM borate solution. The capillary was rinsed with 0.1 NaOH and distilled water, 30 seconds each, and equilibrated with 50 mM borate buffer (for 1 minute) between all injections.

Iothalamate standards were made from Mallinckrodt Medical's 60% Conray (iothalamate meglumine) solution. This was diluted to concentrations of 3, 6, 12, and 24 $\mu$g/ml with 5 mM borate buffer, adjusted with 1.0 N NaOH to pH 11.30. The 5 mM borate was diluted from the stock 50 mM borate buffer. A four point calibration curve was run daily before samples were run. Sample results were automatically calculated from this calibration curve by the System Gold software.

Daily quality control was maintained using stored urine samples from patient samples in the range of 7 to 10 $\mu$g/ml. The urine had been diluted with 5 mM borate and stored at −70°. Samples are stable for at least 2 weeks refrigerated and for six months stored at −70° (20). Plasma controls were made from stored patient samples ranging from 7 to 10 $\mu$g/ml. Undiluted aliquots of 300 $\mu$l were stored in −70° freezer. A control GFR was calculated from urine and plasma control results. The iothalamate run time was adjusted to 3.7±0.05 minutes by altering the kV. $U_0$ was evaluated for evidence of any drug interference having a run time the same as iothalamate. $U_1$ samples were prepared to keep the urine concentration >3.0 and <24.0 µg/ml by rediluting if necessary. The run times for urine and blood were assessed to assure that peak times were within 0.1 minute of each other. GFR calculations were made as follows:

$$\text{Flow} = \frac{\text{Volume } U_1}{\text{Collection time in minutes}} = \text{ml/min}$$

Uncorrected GFR =

$$\frac{U_1 \mu g/ml \times \text{flow ml/min}}{\frac{P_1 + P_2}{2} \mu g/ml^*} = GFR \text{ (ml/min)("cold" iothalamate)}$$

OR

Uncorrected GFR =

$$\frac{U_1 \text{cpm}/2\text{ml} \times \text{flow ml/min}}{\frac{P_1 + P_2}{2} \text{cpm}/2\text{ml}} = GFR(\text{ml/min})(\text{isotopic iothalamate})$$

*$P_1$ and $P_2$ were pooled in equal volumes before deproteinizing resulting in a single $P_1 + P_2$ value. $P_1 + P_2$ value.

GFR is corrected for surface area (S.A.) as follows:

$$\text{Uncorrected } GFR \text{ ml/min} \times \frac{1.73 \, M^2}{S.A. \, [\text{wt. (kg)}^{0.425} \times \text{ht.(cm)}^{0.725} \times .007184]} =$$

Corrected Clearance ml/min/1.73 $M^2$

E. Drug Studies

Prior to the clinical study comparing cold and isotope labeled iothalamate, drug interference studies were carried out. Samples containing known drugs were obtained from the drug laboratory for both blood and urine (Table 1).

TABLE 1

Drugs Tested for Potential Interference (None Found)

Antihypertensives

Calan
Cardine
Cardizem
Labetalol
Lopressor
Minipres
Norvasc
Plendil
Procardia
Propranolol
Tenormin
Vasotec
Diuretics Aldactone
Bumex
Lasix
Maxzide
Endocrine Drugs Insulin
Premarin
Thyroxin
Immunosuppresives Cyclosporine
FK506
Imuran TABLE 1-continued Drugs Tested for Potential Interference (None Found)

Prednisone
Prograf
Miscellaneous

Allopurinol
Etidronate
Fiosol
K-dur
Locoid
Pericolace
Sinemet
Trental
Ursodiol
Analgesics

*Acetaminophen
Ascriptin
Aspirin
Ibuprofen
Meperidine
Naproxen
Propoxyphene
Antibiotics Acyclovir
Nystatin
Psychoactive Drugs Amitriptyline
Amphetamine
Carbamazapine
Desipramine
Diazepam
Diphenydramine
Doxepin
Hydroxyzine
Imipramine
Methamphetamine
Valium
Antihistamines Axid
Phenylpropanolamine
Prilosec
Tripelenamine
Cardioactive Drugs Lanoxin
Persantin
Quinidine
Quinine

*Sulfamethoxazole trimethoprim
*Sulfasalizine
*Drugs with migration times near iothalamate In addition, multiple patient samples were assessed for evidence of interfering substances, and a drug history was taken from 400 patients. From this information, drugs found to have migration times near that of iothalamate were acetaminophen (Tylenol®) and several sulfa preparations, e.g., sulfasalizine and sulfamethoxazole trimethoprim. Multiple alterations of the capillary conditions with alteration of the applied kV and pH were undertaken and successfully separated the drugs from the iothalamate peak. To further assure no interferences from these drugs, a sample cup containing acetaminophen, sulfa, and iothalamate was run assuring that these peaks were separate before analysis of unknown samples. No other interferences were found in over 1000 patient samples. For the purposes of this study, $P_0$ and $U_0$ samples were also obtained and assayed to assure there were no other drugs of concern with identical migration times.

F. Results

Figure 2:
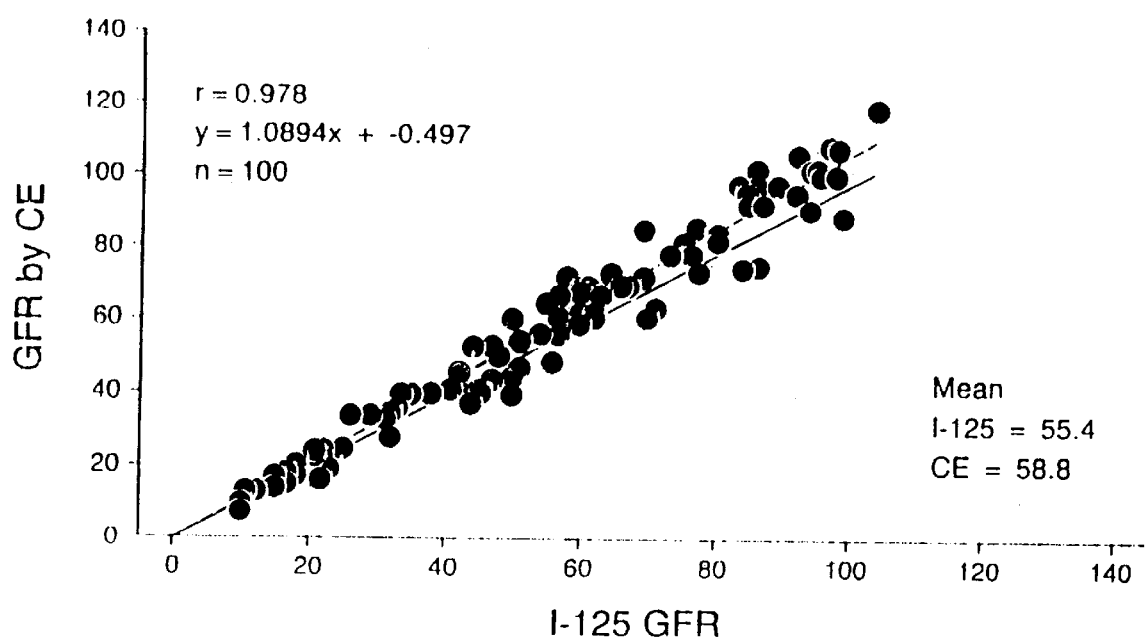
FIG. 2 is a graph depicting the correlation of GFR done by non-isotopic "cold" iothalamate measured by capillary electrophoresis (CE) and "standard" $^{125}$I-iothalamate clearances using a timed urine and the average of 2 plasma samples after subcutaneous injection of the markers.
Figure 3:
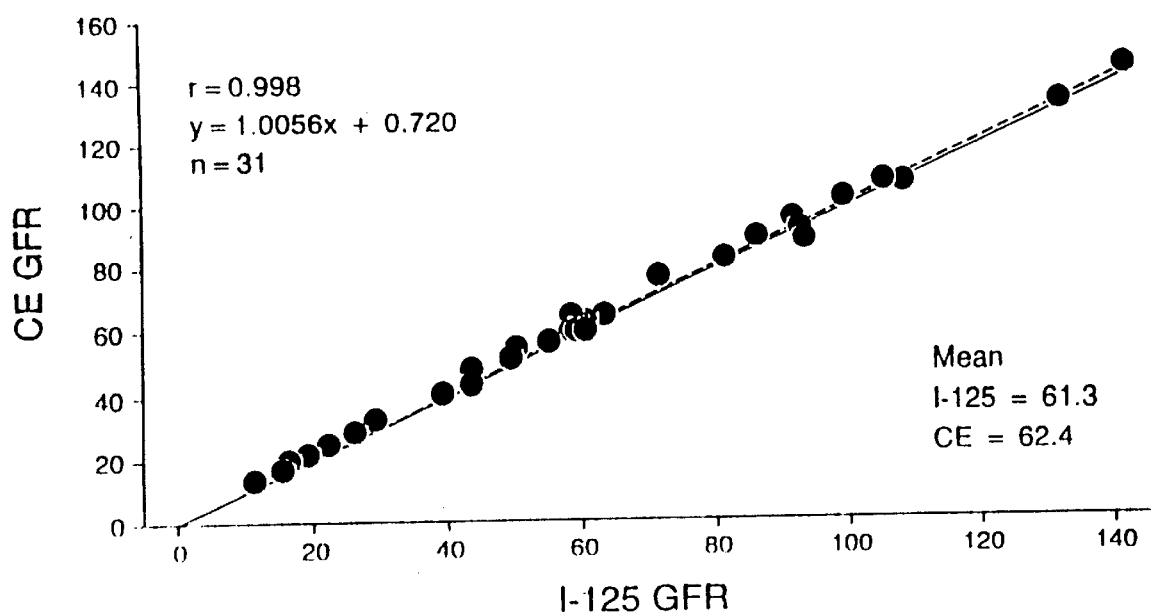
FIG. 3 is a graph depicting the correlation of cold iothalamate with standard $^{125}$I-iothalamate clearances after final technical maneuvers to obviate layering of the ultrafiltrate.

The results of this study showed an excellent correlation of GFR measured by capillary electrophoresis using iothalamate meglumine to GFR obtained using $^{125}$I-iothalamate over a broad range of GFR's (9–103 mls/min/1.73 M$^2$). Correlation coefficient was 0.978 (y=1.089x+−0.50) (FIG. 2). However, the mean GFR was 58 mls/min/1.73 M$^2$ by the present capillary electrophoresis method and 54.4 using the isotope methodology of Ott et al. Although this difference was not significant, further study found it to be related to a false reduction in the plasma level by the capillary electrophoresis method. Additional experimentation led to the conclusion that this reduction was due to a layering effect of plasma samples coming through the filter. The problem was corrected by vortexing the sample after it had been deproteinized as disclosed above. Changing the filtration technique increased the plasma concentration and eliminated the 4 mls/min discrepancy between the 2 techniques so the means in the second group of 31 patients were 62 and 61 mls/min respectively for the two methods (correlation coefficient 0.99) (FIG. 3). The coefficient of variation for the control GFR's over 20 days was 2.85%. Normal values are seen in Table 2. No interfering drugs were seen using the conditions outlined for the capillary electrophoresis methodology.

TABLE 2

Normal Iothalamate Clearance Values*

| AGE | GFR - Range of Normal (ml/min/1.73 m$^2$) |
|---|---|
| 18–22 | >90 |
| 23–27 | >88 |
| 28–32 | >86 |
| 33–37 | >84 |
| 38–42 | >82 |
| 43–47 | >80 |
| 48–52 | >78 |
| 53–57 | >75 |
| 58–62 | >73 |
| >62 | >70 |

*Slack, T. K. and Wilson, D. M.: Normal renal function: C$_{IN}$ and C$_{PAH}$ in healthy donors before and after nephrectomy. Mayo Clin Proc., 51: 296–300, 1976.

The present invention provides a new method for measurement of GFR using a non-isotopic form of iothalamate. The correlation between labeled iothalamate and the CE determined clearance of unlabeled iothalamate is outstanding (r=0.99), and the CV is less than 3%.

The advantage of the small dose of injected iodine required cannot be ignored. The amount of free iodine injected is less than 13 mg, which is less than the amount used to check iodine sensitivity for other radiology procedures (60 mg) and substantially less than the 115 mg given as SSKI (3 drops) to prevent thyroid uptake of $^{125}$I-iothalamate. This avoids the likelihood of iodine sensitivity even for patients with known iodine sensitivity, since this amount is less than that normally injected to check for iodine sensitivity (2 ml). The incidence of sensitivity should compare favorably with the iodine sensitivity for the isotope method.

The establishment of a non-isotopic technique for accurate measure of GFR, which is less expensive and maintains the accuracy of an $^{125}$I-iothalamate clearance, has other advantages. Accommodation for nursing mothers or pregnant women is minimized because the risk of radioisotopes is not a consideration. Furthermore, previous radioisotopic administration for other testing can occasionally interfere with $^{125}$I-iothalamate GFR measurements. This is not a problem using the present capillary electrophoresis method. If Conray® has been used for a radiologic study, the GFR will be calculated with higher amounts in the urine and blood and does not degrade the quality of the result. Furthermore, shelf life of the "cold" iothalamate is not a problem, and radioisotope disposal and restrictions for mailing samples are avoided. Therefore, costs for clinical trials should be markedly reduced, and more precise GFR measurements are feasible for individual practices. Practices without access to CE technology can use a reference laboratory by injecting and collecting appropriate samples and submitting them for analysis using the present kits.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for determining glomerular filtration rate in a mammal comprising:
   (a) subcutaneously administering to said mammal an effective detection amount of an iothalamic acid salt;
   (b) obtaining a first blood plasma sample from said mammal;
   (c) measuring the volume of urine produced by said mammal over a preselected period of time following said administration;
   (d) obtaining a second blood plasma sample from said mammal;
   (e) employing capillary electrophoresis to measure the concentration of said iothalamic acid salt in said first and second plasma samples and in a sample of said urine;
   (f) determining the urinary flow rate over said period of time; and
   (g) calculating the glomerular filtration rate by dividing the concentration of said iothalamic acid salt in said urine sample multiplied by the flow rate, by the average of the concentrations of said iothalamic acid salt in said plasma samples.

2. The method of claim 1 wherein water is administered to said mammal prior to step (a).

3. The method of claim 1 wherein water is administered to said mammal during at least one of steps (a), (b) or (c).

4. The method of claim 1 wherein a maximal blood level of said iothalamic acid salt is reached prior to said preselected period of time.

5. The method of claim 1 further comprising correcting the glomerular filtration rate for the body area of the mammal.

6. The method of claim 1 wherein the mammal is a human.

7. The method of claim 1 wherein the iothalamic acid salt is iothalamate meglumine.

8. The method of claim 1 wherein said plasma samples are deproteinized prior to step (e).

9. The method of claim 1 wherein the urine sample is deproteinized prior to step (e).

10. A method for determining glomerular filtration rate in a human comprising:
    (a) subcutaneously administering to said human an effective detection amount of iothalamate meglumine;
    (b) obtaining a first blood plasma sample from said human;

(c) measuring the volume of urine produced by said human over a preselected period of time following said administration;

(d) obtaining a second blood plasma sample from said human;

(e) employing capillary electrophoresis to measure the concentration of said iothalamate meglumine in said first and second plasma samples and in a sample of said urine;

(f) determining the urinary flow rate over said period of time; and (g) calculating the glomerular filtration rate by dividing the concentration of said iothalamate meglumine in said urine multiplied by the flow rate by the average of the concentrations of said iothalamate meglumine in said plasma samples.

11. The method of claim 10 wherein water is administered to said human prior to step (a).

12. The method of claim 10 wherein water is administered to said human during at least one of steps (a), (b) or (c).

13. The method of claim 10 wherein a maximal blood level of said iothalamate meglumine is reached prior to said preselected period of time.

14. The method of claim 10 further comprising correcting the glomerular filtration rate for the body area of the human.

15. The method of claim 10 wherein said plasma samples are deproteinized prior to step (e).

16. The method of claim 10 wherein said urine sample is deproteinized prior to step (e).

17. A method for determining glomerular filtration rate in a human comprising:

(a) subcutaneously administering to said human an effective detection amount of iothalamate meglumine;

(b) measuring the volume of urine produced by said human over a preselected period of time following said administration;

(c) obtaining a sample of blood plasma from said human at about the midpoint of said period of time;

(d) employing capillary electrophoresis to measure the concentration of said iothalamate meglumine in said plasma sample and in a sample of said urine;

(e) determining said urinary flow rate over said period of time; and (f) calculating the glomerular filtration rate by dividing the concentration of said iothalamate meglumine in said urine sample multiplied by said urinary flow rate by the concentration of said iothalamate meglumine in said plasma sample.

18. The method of claim 17 wherein water is administered to said human prior to step (a) or during at least one of steps (a) or (b).

19. The method of claim 17 wherein the iothalamate meglumine is administered by subcutaneous injection.

20. The method of claim 17 wherein a maximal blood level of said iothalamate meglumine is reached prior to said preselected period of time.

21. The method of claim 17 wherein said plasma sample and said urine sample are deproteinized prior to step (d).

* * * * *